US012758748B2

(12) United States Patent
Fuller et al.

(10) Patent No.: US 12,758,748 B2
(45) Date of Patent: Oct. 13, 2026

(54) INTRAVASCULAR IMAGING CATHETER

(71) Applicant: Boston Scientific Scimed, Inc., Maple Grove, MN (US)

(72) Inventors: Jeffrey Steven Fuller, Brooklyn Park, MN (US); Quinn Mackenzie Butler, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 158 days.

(21) Appl. No.: 18/586,680

(22) Filed: Feb. 26, 2024

(65) Prior Publication Data

US 2024/0285912 A1 Aug. 29, 2024

Related U.S. Application Data

(60) Provisional application No. 63/448,554, filed on Feb. 27, 2023.

(51) Int. Cl.
*A61M 25/00* (2006.01)
*A61M 25/09* (2006.01)
*G06T 1/00* (2006.01)

(52) U.S. Cl.
CPC ........ *A61M 25/09* (2013.01); *A61M 25/0023* (2013.01); *G06T 1/0007* (2013.01); *A61M 2025/091* (2013.01)

(58) Field of Classification Search
CPC .............. A61M 25/09; A61M 25/0023; A61M 2025/091; A61M 25/0051; A61M 25/0052; G06T 1/0007; A61B 5/0084; A61B 5/6852; A61B 8/12; A61B 5/0066; A61B 8/0891; A61B 8/445
See application file for complete search history.

(56) References Cited

U.S. PATENT DOCUMENTS

| | | | |
|---|---|---|---|
| 5,772,609 | A | 6/1998 | Nguyen et al. |
| 6,139,510 | A | 10/2000 | Palermo |
| 8,728,010 | B2 | 5/2014 | Hirshman |
| 9,474,506 | B2 | 10/2016 | Magnin et al. |
| 2004/0181174 | A2 | 9/2004 | Davis et al. |
| 2005/0215942 | A1 | 9/2005 | Abrahamson et al. |
| 2007/0066900 | A1 | 3/2007 | O'Keeffe |
| 2012/0059241 | A1 | 3/2012 | Hastings et al. |

(Continued)

FOREIGN PATENT DOCUMENTS

EP 2844135 B1 6/2022

OTHER PUBLICATIONS

International Search Report and Written Opinion for International Application No. PCT/US2024/017209, dated Jun. 11, 2024. (12 pages).

*Primary Examiner* — Joel Lamprecht
(74) *Attorney, Agent, or Firm* — SEAGER, TUFTE & WICKHEM, LLP

(57) ABSTRACT

Intravascular imaging devices as well as methods for making and using intravascular imaging devices are disclosed. An intravascular imaging device, may include a catheter shaft assembly including a telescoping assembly and a catheter body. The catheter body may include a hypotube region, an imaging window region, and a distal end region having a guidewire lumen formed therein. At least a portion of the hypotube region may have a plurality of slots formed therein. An imaging core may be disposed within the catheter shaft assembly.

20 Claims, 8 Drawing Sheets

(56) References Cited

U.S. PATENT DOCUMENTS

| | | | | |
|---|---|---|---|---|
| 2014/0171804 | A1 | 6/2014 | Van Hoven | |
| 2014/0180031 | A1 | 6/2014 | Anderson | |
| 2014/0180122 | A1* | 6/2014 | Stigall | A61B 5/6852 600/478 |
| 2014/0276109 | A1* | 9/2014 | Gregorich | A61B 5/0215 600/478 |
| 2017/0164925 | A1 | 6/2017 | Marshall et al. | |
| 2020/0061340 | A1* | 2/2020 | Mixter | A61B 8/4466 |
| 2020/0121280 | A1* | 4/2020 | Marshall | A61B 8/0891 |

* cited by examiner

INTRAVASCULAR IMAGING CATHETER

CROSS-REFERENCE TO RELATED APPLICATIONS

This application claims the benefit of priority under 35 U.S.C. § 119 of U.S. Provisional Application No. 63/448,554, filed Feb. 27, 2023, the entire disclosure of which is hereby incorporated by reference.

TECHNICAL FIELD

The present disclosure pertains to medical devices, and methods for manufacturing medical devices. More particularly, the present disclosure pertains to intravascular imaging catheters.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An intravascular imaging device is disclosed. The intravascular imaging device comprises: a catheter shaft assembly including a telescoping assembly and a catheter body; wherein the catheter body includes a hypotube region, an imaging window region, and a distal end region having a guidewire lumen formed therein; wherein at least a portion of the hypotube region has a plurality of slots formed therein; and an imaging core disposed within the catheter shaft assembly.

Alternatively or additionally to any of the embodiments above, the imaging core is translatable within the catheter shaft assembly.

Alternatively or additionally to any of the embodiments above, the imaging core includes an ultrasound transducer.

Alternatively or additionally to any of the embodiments above, the imaging core includes an optical coherence tomography imaging device.

Alternatively or additionally to any of the embodiments above, a distal portion of the hypotube region has the plurality of slots formed therein.

Alternatively or additionally to any of the embodiments above, the plurality of slots are disposed along a section of the hypotube region that is 5-50 cm from a distal end of the hypotube region.

Alternatively or additionally to any of the embodiments above, the plurality of slots are disposed along a section of the hypotube region that is 8-39 cm from a distal end of the hypotube region.

Alternatively or additionally to any of the embodiments above, a proximal portion of the hypotube region is free of slots.

Alternatively or additionally to any of the embodiments above, at least some of the slots of the plurality of slots lie within a plane that is substantially normal to a longitudinal axis of the hypotube region.

Alternatively or additionally to any of the embodiments above, the plurality of slots are arranged in a helical pattern.

Alternatively or additionally to any of the embodiments above, a proximal end region of the imaging window region is disposed along an outer surface of the hypotube region.

Alternatively or additionally to any of the embodiments above, a proximal end region of the imaging window region is disposed along an inner surface of the hypotube region.

Alternatively or additionally to any of the embodiments above, a proximal end of the imaging window region abuts a distal end of the hypotube region.

Alternatively or additionally to any of the embodiments above, a sleeve is disposed over the proximal end of the imaging window and the distal end of the hypotube region.

An intravascular imaging device is disclosed. The intravascular imaging device comprises: a catheter shaft assembly including a telescoping assembly and a catheter body; wherein the catheter body includes a hypotube attached to the telescoping region, an imaging window region extending distally from the hypotube, and a distal end region having a guidewire lumen formed therein; wherein the hypotube has a distal region having plurality of slots formed therein and a proximal region free from slots; and an imaging core disposed within the catheter shaft assembly.

Alternatively or additionally to any of the embodiments above, a proximal end region of the imaging window region is disposed along an outer surface of the hypotube.

Alternatively or additionally to any of the embodiments above, the plurality of slots are arranged so that at least some of the slots lie within a plane that is substantially normal to a longitudinal axis of the hypotube.

Alternatively or additionally to any of the embodiments above, the plurality of slots are arranged in a helical pattern.

Alternatively or additionally to any of the embodiments above, the plurality of slots are arranged in a spiral pattern.

A method for imaging a blood vessel is disclosed. The method comprises: disposing an intravascular imaging device within a blood vessel, the intravascular imaging device comprising: a catheter shaft assembly including a telescoping assembly and a catheter body, wherein the catheter body includes a hypotube attached to the telescoping region, an imaging window region extending distally from the hypotube, and a distal end region having a guidewire lumen formed therein, wherein the hypotube has a distal region having plurality of slots formed therein and a proximal region free from slots, and an imaging core disposed within the catheter shaft assembly; and translating the imaging core relative to the catheter shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
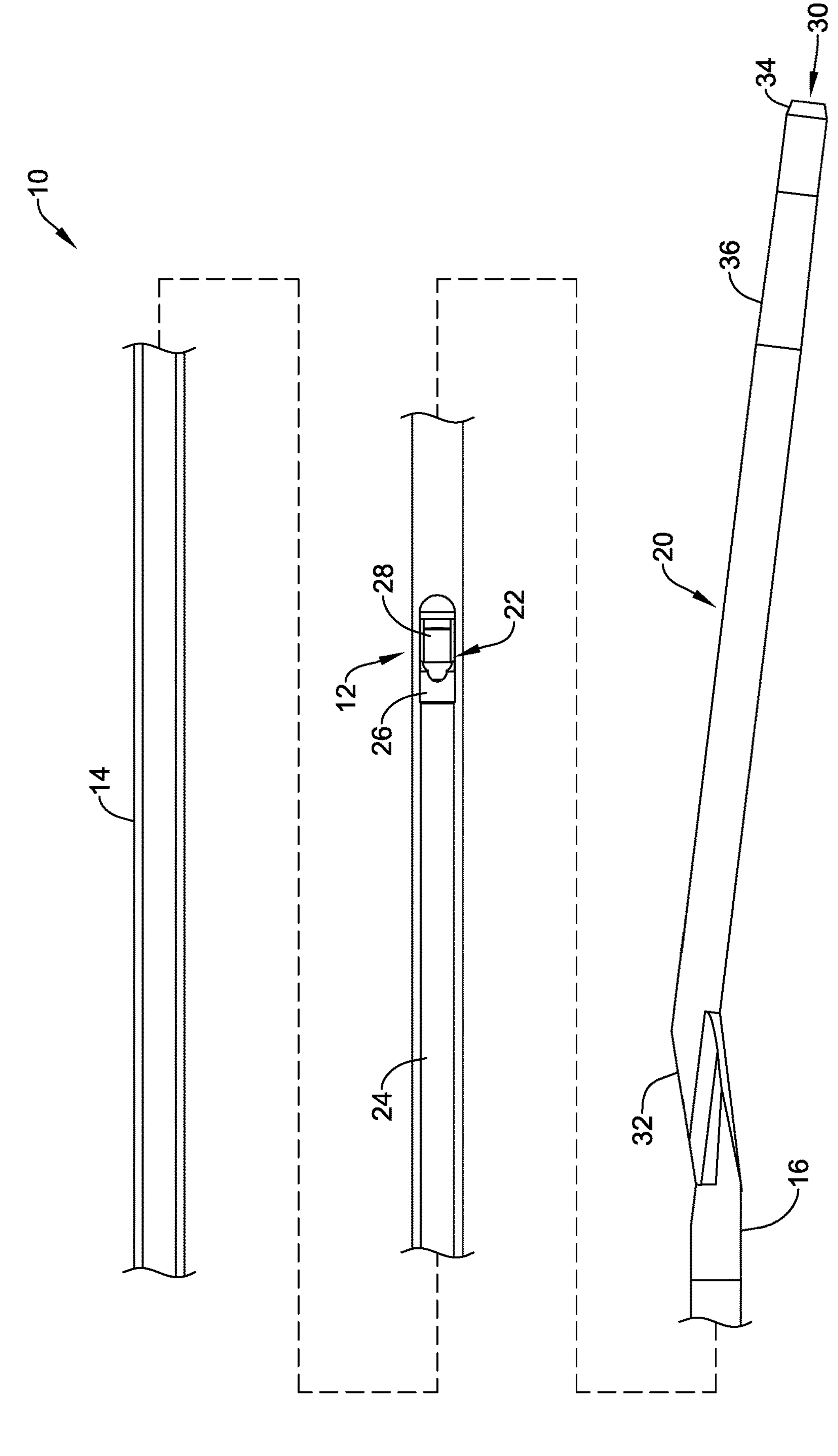
FIG. 1 is a side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a side view of a portion of example medical device 10. In at least some instances, the medical device 10 takes the form of an imaging medical device. For example, the medical device 10 may be an intravascular ultrasound (IVUS) device that may be used to image a blood vessel. In some of these and in other instances the medical device may be an optical coherence tomography (OCT) imaging device, a near-infrared spectroscopy (NIRS) imaging device, near-infrared fluorescence (NIRF) imaging device, a photoacoustic imaging device, a fluorescence-lifetime imaging device, combinations thereof, and/or the like. The structure/form of the medical device 10 can vary. In some instances, the medical device 10 may include an elongate shaft 12 having a proximal end region 14 and a distal end region 16. A tip member 20 may be coupled to or otherwise disposed adjacent to the distal end region 16. The tip member 20 may include a guidewire lumen 30 having a guidewire exit port 32, an atraumatic distal end 34, one or more radiopaque markers 36, and/or other features. In some embodiments, the tip member 20 may extend at a non-parallel angle to the proximal end region 14 of the elongate shaft 12.

An imaging assembly 22 (e.g., which may sometime be referred to as an imaging core) may be disposed within a lumen of the elongate shaft 12. In general, the imaging assembly 22 may be used to capture/generate images of a blood vessel. In some instances, the medical device may include devices and/or features similar to those disclosed in U.S. Patent Application Pub. No. US 2012/0059241 and U.S. Patent Application Pub. No. US 2017/0164925, the entire disclosures of which are herein incorporated by reference. In at least some instances, the medical device 10 may resemble and/or include features that resemble the OPTICROSS™ Imaging Catheter, commercially available from BOSTON SCIENTIFIC, Marlborough, MA.

The imaging assembly 22 may include a drive shaft or cable 24, a housing 26, and an imaging member or transducer 28 coupled to the drive shaft 24 and/or housing 26. In at least some instances, the transducer 28 includes an ultrasound transducer. Other transducers are also contemplated. The transducer 28 may be rotatable and/or axially translatable relative to the elongate shaft 12. For example, the drive shaft 24 may be rotated and/or translated in order to rotate and/or translate the transducer 28 (and the housing 26).

Figure 2:
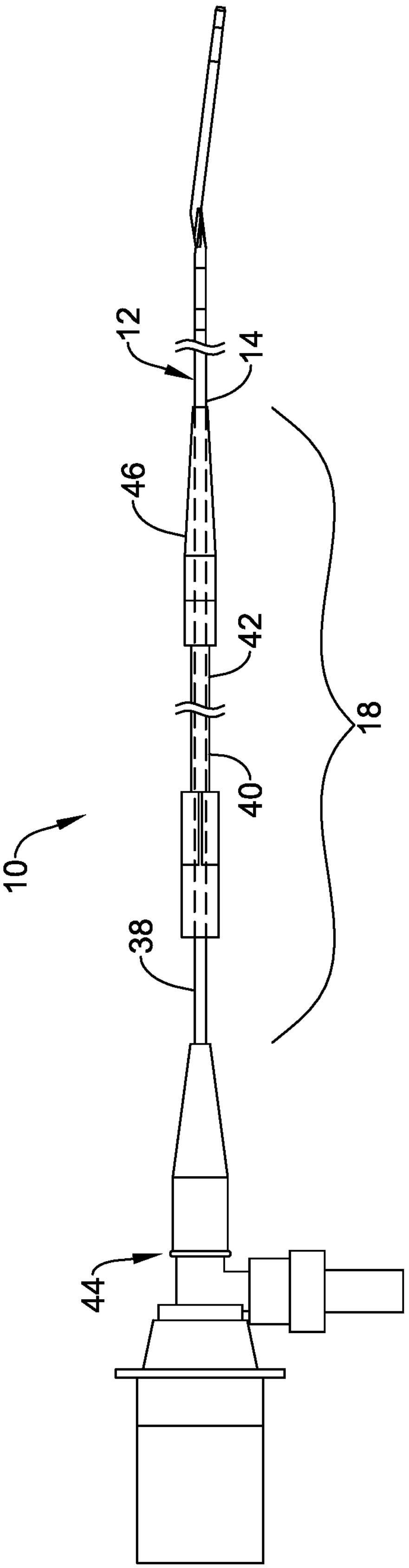
FIG. 2 is a side view of an example medical device.

The proximal end region 14 of the elongate shaft 12 may be coupled to a telescoping assembly 18 as shown in FIG. 2. In general, the telescoping assembly 18 may be configured to allow the medical device operator to move the drive shaft 24 including the imaging assembly 22 proximally and distally within the catheter (e.g., relative to the elongate shaft 12), without having to move the entire catheter within the patient. This allows the catheter operator to easily change the location of the imaging assembly or other medical device within the patient. For example, the telescoping assembly 18 may be actuated to change the location of the imaging assembly 22 within the elongate shaft 12.

The proximal end region 14 of the elongate shaft 12 may be coupled to the telescoping assembly 18. For example, the proximal end region 14 of the elongate shaft 12 may be coupled to a distal hub 46 of the telescoping assembly 18. A proximal hub 44 may be coupled to the telescoping assembly 18 (e.g., at the proximal end of the telescoping assembly 18). The drive shaft 24 (see FIG. 1) may extend through the telescoping assembly 18 and be coupled to and/or otherwise secured to the proximal hub 44.

The telescoping assembly 18 may include a first sheath 38 and a second sheath 40. In some instances, the first sheath 38 may be understood to be an inner telescoping tube 38 and the second sheath 40 may be understood to be an outer telescoping tube 40. Generally, the outer telescoping tube 40 may be disposed over the inner telescoping tube 38. The inner telescoping tube 38 may be coupled to or otherwise secured to the proximal hub 44. The outer telescoping tube 40 may be coupled or otherwise secured to the distal hub 46. The inner telescoping tube 38 may be axially and/or rotatably moveable relative to the outer telescoping tube 40. Because the drive shaft 24 may be secured to the proximal hub 44 and/or the inner telescoping tube 38 and because the elongate shaft 12 may be secured to the distal hub 46, movement of the proximal hub 44 relative to the distal hub 46 results in movement of the inner telescoping tube 38 and the drive shaft 24 relative to the distal hub 46 and/or the elongate shaft 12.

In use, the elongate shaft 12 may be disposed within a target region (e.g., a blood vessel) and the imaging assembly 22 may be translated within the elongate shaft 12 in order to image the blood vessel. It can be appreciated that navigating the elongate shaft 12 through the vasculature toward the target region may include navigating the elongate shaft 12 through a number of tortuous bends and turns. As such, it may be desirable for the elongate shaft 12 to be sufficiently flexible in order to navigate such anatomy. Furthermore, it may be desirable for the elongate shaft 12 to be sufficiently pushable (e.g., in a manner that resists buckling) and be capable of transmitting torque along the length of the elongate shaft 12. Disclosed herein are medical devices (e.g., such as the medical device 10) where the elongate shaft 12 is designed to have a desirable level of flexibility, pushability, torquability, and/or other characteristics.

Figure 3:
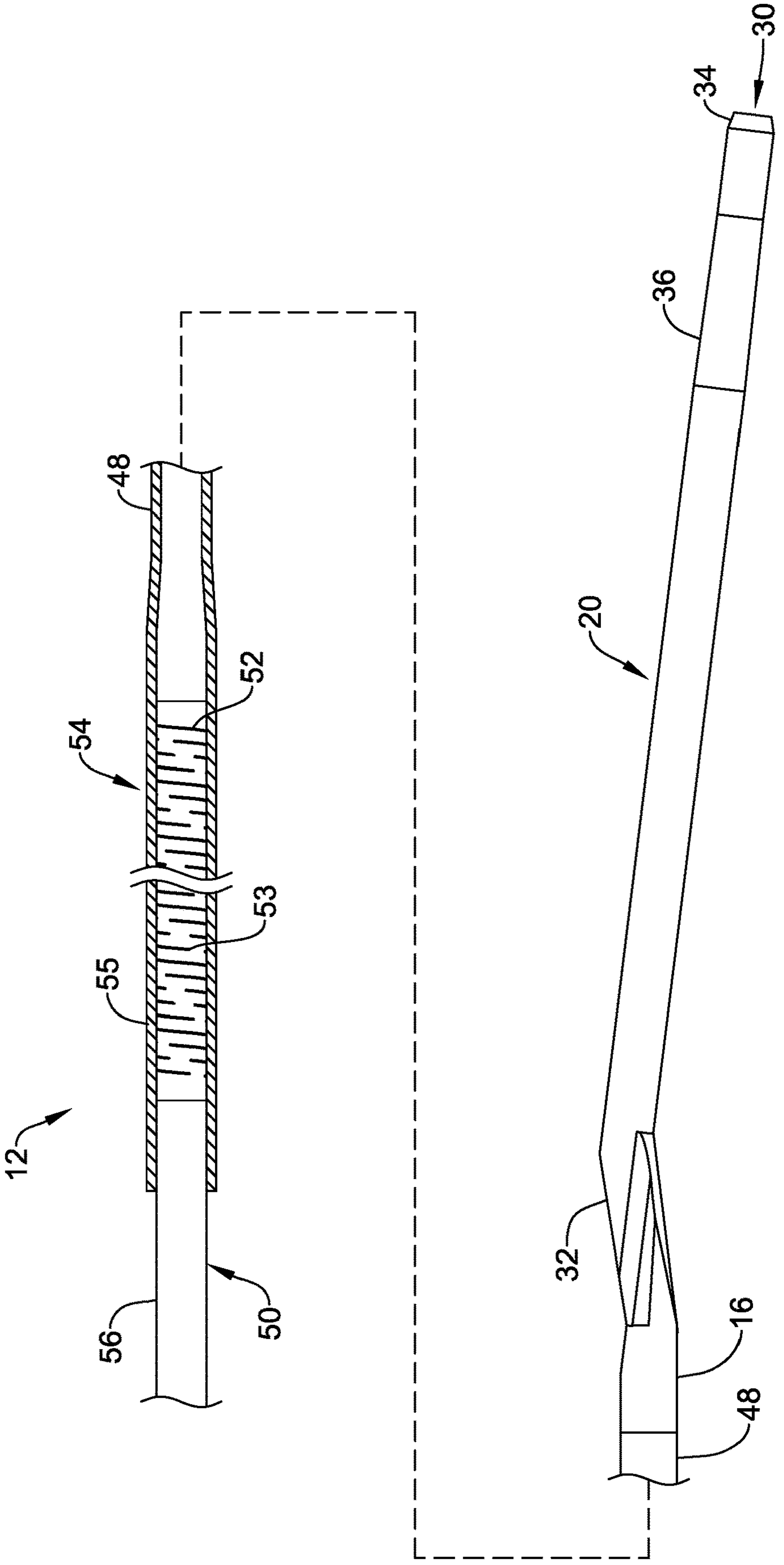
FIG. 3 is a partial cross-sectional side view of a portion of an example medical device.

FIG. 3 illustrate a portion of the elongate shaft 12. As shown and described, the elongate shaft 12 may be an assembly of different parts/regions (e.g., the elongate shaft 12 may be understood to be an elongate shaft assembly or catheter shaft assembly). For example, the elongate shaft 12 may include an imaging window region 48. As the name suggests, the imaging window region 48 is a region of the elongate shaft 12 through which the imaging assembly 22 (e.g., the transducer 28) can image through. While the imaging assembly 22 is not shown in FIG. 3, it can be appreciated that the imaging assembly 22 may be disposed within the elongate shaft 12 in the manner depicted in FIG. 1, for example. The imaging window region 48 may have a distal end that is coupled to and/or otherwise disposed adjacent to the tip member 20. In some instances, the imaging window region 48 extend the full length of the elongate shaft 12 (e.g., the full length proximally from the tip member 20). In other instances, the imaging window region 48 may extend along a portion of the elongate shaft 12. For example, the imaging window region 48 may have a length of about 5-50 cm, or about 10-30 cm, or about 15-25 cm, or about 20-22 cm. The imaging window region 48 may be formed from a suitable material such as nylon, nylon-12, polyether block amide, combinations thereof, and/or other suitable materials including those materials disclosed herein.

The elongate shaft 12 may also include a hypotube region 50. The hypotube region 50 may extend proximally from the imaging window region 48 to the distal hub 46. The hypotube region 50 and the imaging window region 48 may be coupled together at a joint 54. In some instances, the joint 54 may be defined by or otherwise include an overlap between the proximal end/region of the imaging window region 48 and the distal end/region of the hypotube region 50. In some instance, the amount of overlap may have a length. For example, the length of the overlap may be on the order of about 1 cm to about 50 cm, or about 5-45 cm, or about 8-42 cm, or about 8-39 cm.

In some instances, the joint 54 may be formed by tapering the proximal end region of the imaging window region 48 so that the imaging window region 48 may be fitted over or otherwise disposed along the outer surface of the hypotube region 50. This may include increasing the inner diameter and/or the outer diameter of the imaging window region 48 in order to allow for the imaging window region 48 to be fitted over the hypotube region 50. In some instances, the wall thickness of the imaging window region 48 by be thinned (e.g., thereby increasing the inner diameter of the imaging window region 48). In some of these and in other instances, the outer diameter and the inner diameter of the imaging window region 48 may be increased.

The hypotube region 50 may have a plurality of slots 52 formed therein. The slots 52 may help to provide a desirable level of flexibility (and/or pushability and/or torqueability) of the elongate shaft 12. Various arrangements and configurations are contemplated for slots 52. For example, in some embodiments, at least some, if not all of the slots 52 are disposed at the same or a similar angle with respect to the longitudinal axis of the hypotube region 50. In some instances, the slots 52 can be disposed at an angle that is perpendicular, or substantially perpendicular, and/or can be characterized as being disposed in a plane that is normal to the longitudinal axis of the hypotube region 50. However, in other instances, the slots 52 can be disposed at an angle that is not perpendicular, and/or can be characterized as being disposed in a plane that is not normal to the longitudinal axis of the hypotube region 50. This may include angled slots 52, slots 52 arranged in a spiral or helical pattern/arrangement, and/or the like. Additionally, a group of one or more slots 52 may be disposed at different angles relative to another group of one or more slots 52. The distribution and/or configuration of the slots 52 can also include, to the extent applicable, any of those disclosed in U.S. Pat. Publication No. US 2004/0181174, the entire disclosure of which is herein incorporated by reference.

The slots 52 can be formed by methods such as micro-machining, saw-cutting (e.g., using a diamond grit embedded semiconductor dicing blade), electrical discharge machining, grinding, milling, casting, molding, chemically etching or treating, or other known methods, and the like. In at least some embodiments, the slots 52 may be formed in tubular member using a laser cutting process. The laser cutting process may include a suitable laser and/or laser cutting apparatus. For example, the laser cutting process may utilize a fiber laser.

In some instances, the slots 52 disposed along a slotted section 53 of the hypotube region 50 that extends about 5-50 cm from a distal end of the hypotube region 50, or that extends about 8-39 cm from the distal end of the hypotube region 50. In other words, the length of the slotted section 53 of the hypotube region 50 may be about 5-50 cm or about 8-39 cm. In some instances, a proximal section 56 of the hypotube region 50 may be free from slots. In some instances, the shaft 12 may include a relatively short (e.g., on the order of about 1-50 mm) tubular section that is free of slots. This unslotted tubular section may be coupled to and/or otherwise integrally formed with the hypotube region 50. In such constructions, the shaft may lack the slotted section 53.

In some instances, the joint 54 and/or the imaging window region 48 may overlap with at least some of the slots 52. For example, the overlapping portion 55 of the imaging window region 48 that overlaps with the hypotube region 50 may cover some or all of the slots 52. In some instances, it may be desirable for the overlapping portion 55 to overalap all of the slots 52, for example, so as to seal the slotted section 53. In some instances, the overlapping portion 55 of the imaging window region 48 that overlaps with the hypotube region 50 may extend about 1-100 mm, or about 10-50 mm, or about 20-40 mm, or about 30 mm proximally of the most proximal slot 52. Other arrangements are contemplated.

Figure 4:
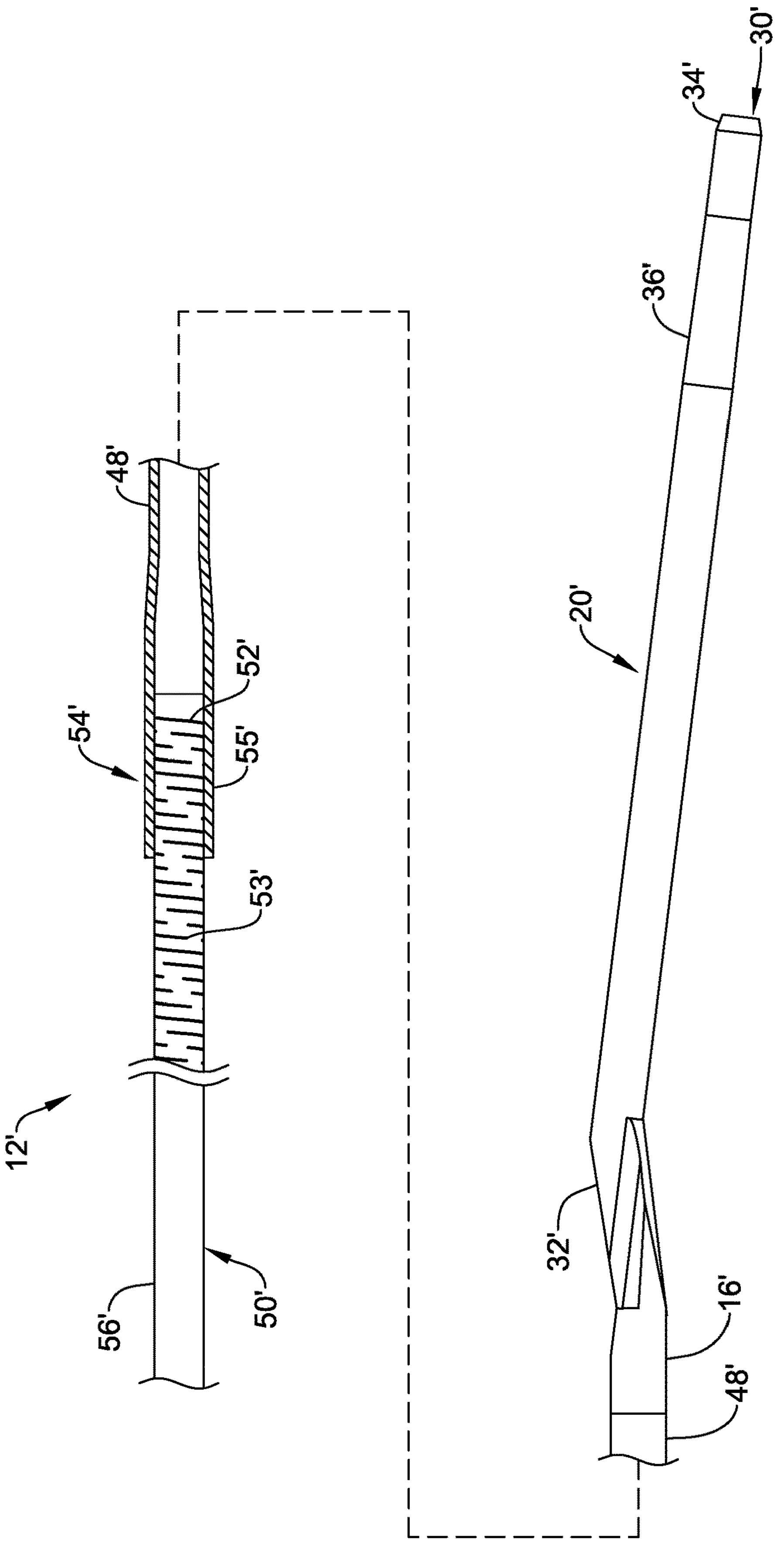
FIG. 4 is a partial cross-sectional side view of a portion of an example medical device.

FIG. 4 illustrates another example elongate shaft 12' that may be similar in form and function to the elongate shaft 12. The elongate shaft 12' may include a distal end region 16'.

A tip member 20' may be coupled to or otherwise disposed adjacent to the distal end region 16'. The tip member 20' may include a guidewire lumen 30' having a guidewire exit port 32', an atraumatic distal end 34', one or more radiopaque markers 36', and/or other features. The elongate shaft 12' may include an imaging window region 48' and a hypotube region 50'. The hypotube region 50' may include a slotted section 53' having a plurality of slots 52' formed therein. A joint 54' is formed between the hypotube region 50' and the imaging window region 48'. In the example shown in FIG. 4, the overlapping portion 55' of the imaging window region 48' overlaps with some, but not all, of the slots 52'. In some instances, the inner surface and/or outer surface of the slotted section 53' may include a sleeve, coating, and/or seal that may close off or seal slots 52' not covered by the overlapping portion 55'. A proximal section 56' of the hypotube region 50' may be free of slots.

Figure 5:
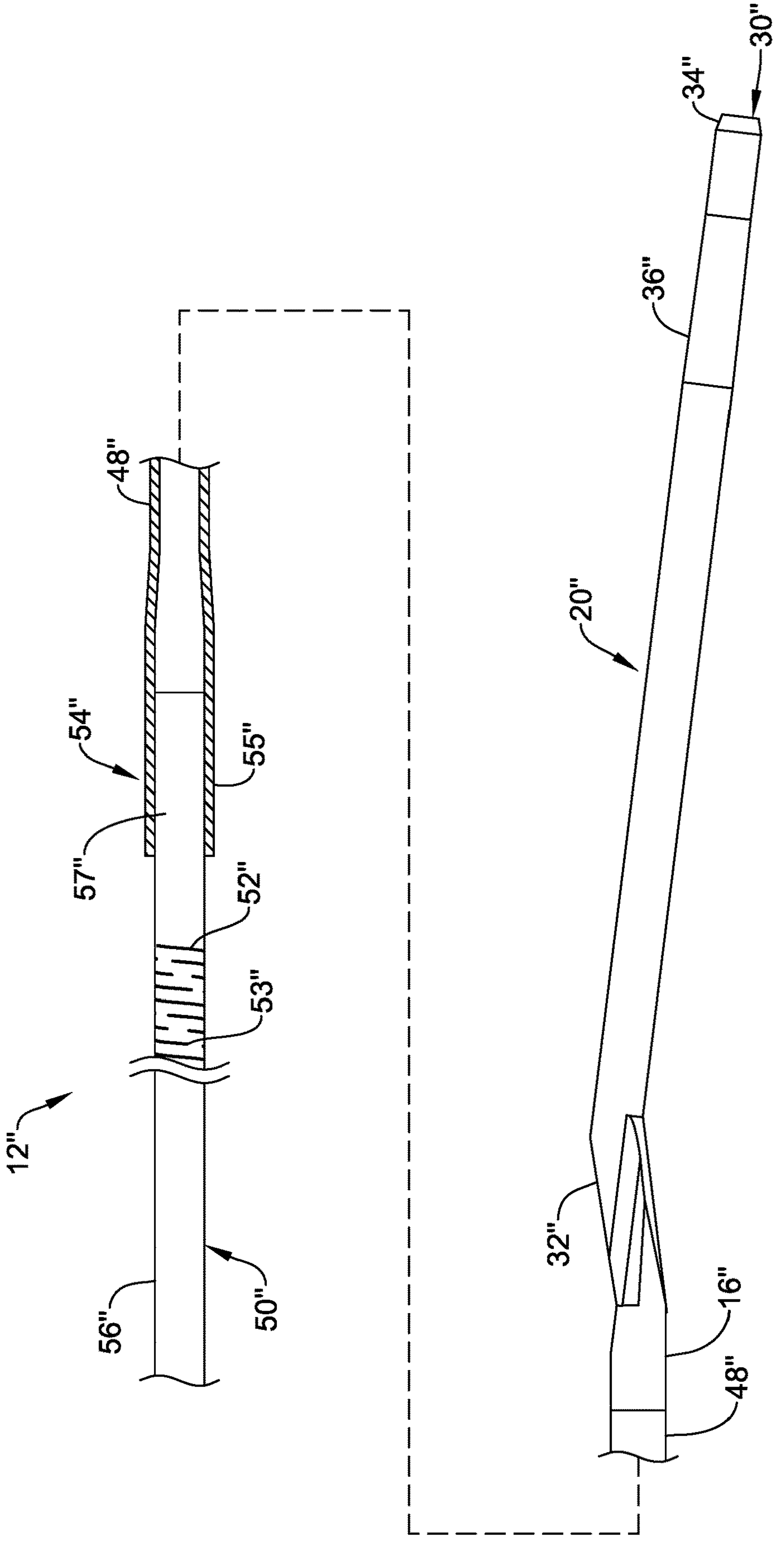
FIG. 5 is a partial cross-sectional side view of a portion of an example medical device.

FIG. 5 illustrates another example elongate shaft 12" that may be similar in form and function to other elongate shafts disclosed herein. The elongate shaft 12" may include a distal end region 16". A tip member 20" may be coupled to or otherwise disposed adjacent to the distal end region 16". The tip member 20" may include a guidewire lumen 30" having a guidewire exit port 32", an atraumatic distal end 34", one or more radiopaque markers 36", and/or other features. The elongate shaft 12" may include an imaging window region 48" and a hypotube region 50". The hypotube region 50" may include a slotted section 53" having a plurality of slots 52" formed therein. A joint 54" is formed between the hypotube region 50" and the imaging window region 48". In the example shown in FIG. 5, the overlapping portion 55" of the imaging window region 48" does not overlap with the slots 52". In other words, the overlapping portion 55" of the imaging window region 48" is disposed distally of the slots 52". In some instances, the inner surface and/or outer surface of the slotted section 53" may include a sleeve, coating, and/or seal that may close off or seal slots 52" not covered by the overlapping portion 55". A non-slotted distal region 57" of the hypotube region 50" may be covered by the overlapping portion 55". A proximal section 56" of the hypotube region 50" may be free of slots.

Figure 6:
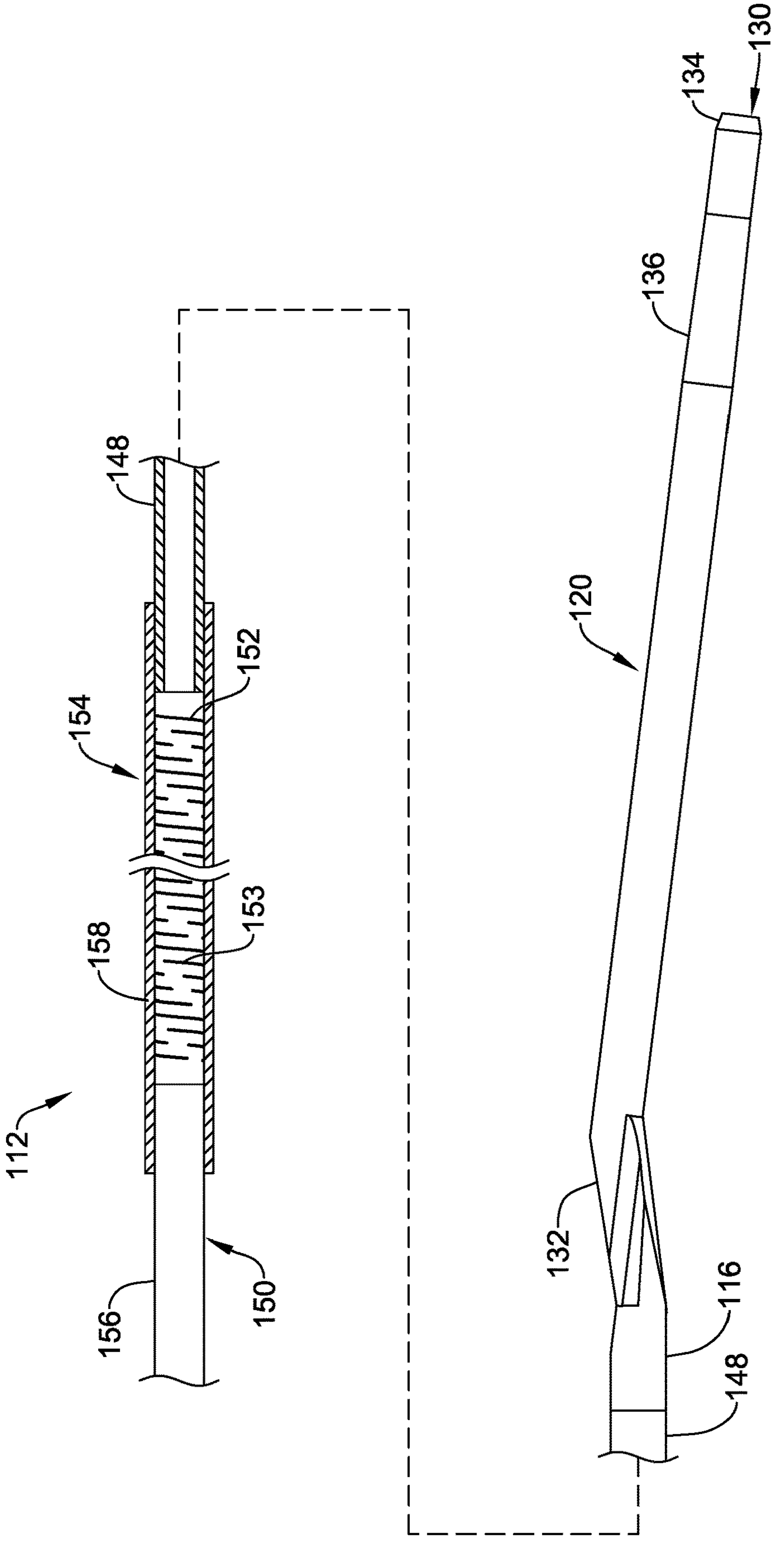
FIG. 6 is a partial cross-sectional side view of a portion of an example medical device.

FIG. 6 illustrates another example elongate shaft 112 that may be similar in form and function to other elongate shafts disclosed herein. The elongate shaft 112 may include a distal end region 116. A tip member 120 may be coupled to or otherwise disposed adjacent to the distal end region 116. The tip member 120 may include a guidewire lumen 130 having a guidewire exit port 132, an atraumatic distal end 134, one or more radiopaque markers 136, and/or other features. The elongate shaft 112 may include an imaging window region 148 and a hypotube region 150. The hypotube region 150 may include a slotted section 153 having a plurality of slots 152 formed therein. A joint 154 is formed between the hypotube region 150 and the imaging window region 148. In the example shown in FIG. 6, the joint 154 is formed by abutting the hypotube region 150 with the imaging window region 148 and disposing a securing member or sheath 158 over the ends of the hypotube region 150 with the imaging window region 148 to secure the hypotube region 150 with the imaging window region 148. A proximal section 156 of the hypotube region 150 may be free of slots.

Figure 7:
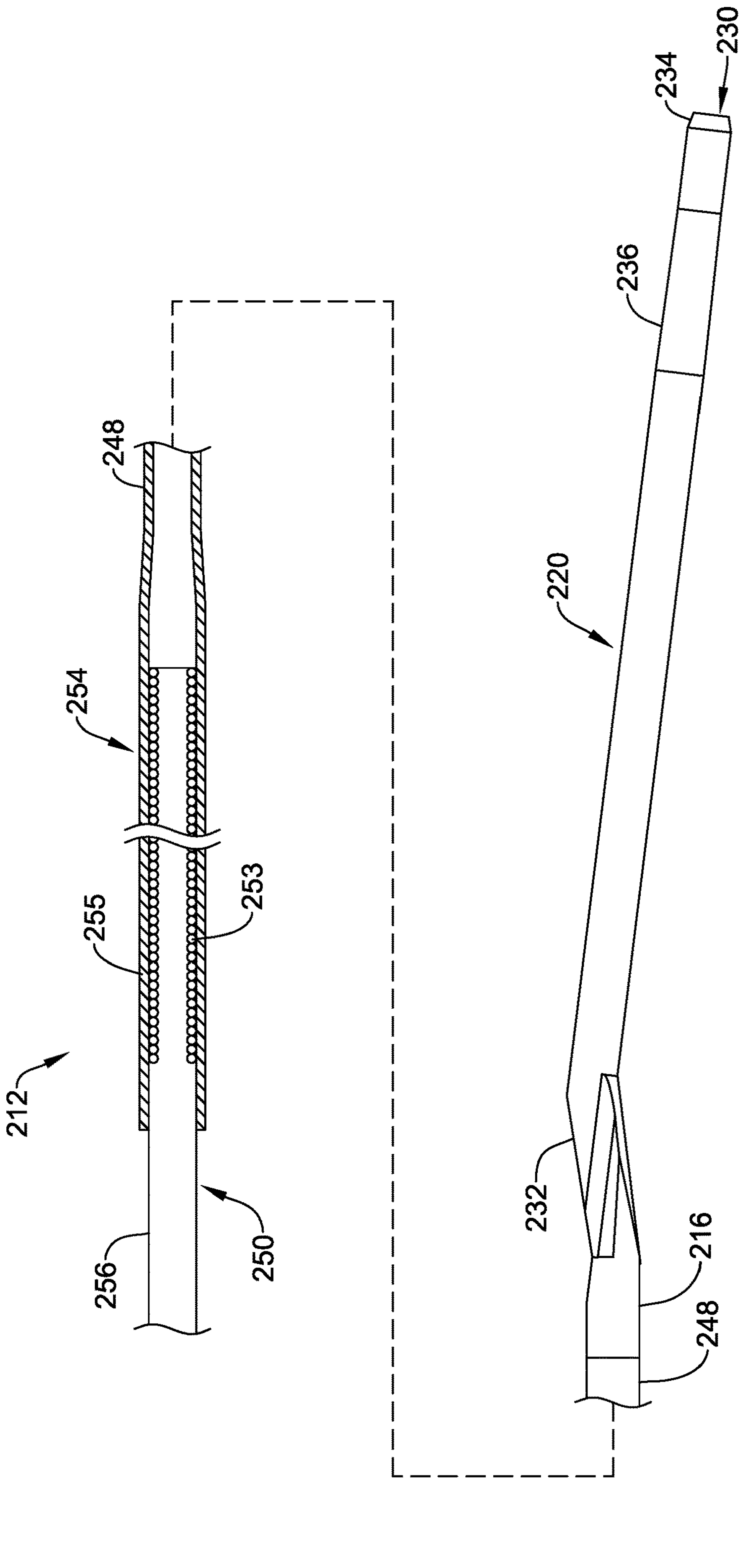
FIG. 7 is a partial cross-sectional side view of a portion of an example medical device.

FIG. 7 illustrates another example elongate shaft 212 that may be similar in form and function to other elongate shafts disclosed herein. The elongate shaft 212 may include a distal end region 216. A tip member 220 may be coupled to or otherwise disposed adjacent to the distal end region 216. The tip member 220 may include a guidewire lumen 230 having a guidewire exit port 232, an atraumatic distal end 234, one or more radiopaque markers 236, and/or other features. The elongate shaft 212 may include an imaging window region 248 and a hypotube region 250. The hypotube region 250 may include a coiled section 253. In some instances, the coiled section 253 may be formed from a wire having a substantially circular cross-sectional shape. In other instances, the coiled section 253 may be formed from a ribbon or otherwise formed from a wire having a non-circular (e.g., rectangular) cross-sectional shape. In other instances, the coiled section 253 may be formed from a spiral cut hypotube (e.g., which may be cut in a manner that may resemble a coil or a coil-like structure). A joint 254 is formed between the hypotube region 250 and the imaging window region 248. In the example shown in FIG. 7, the joint 254 is formed by overlapping an overlapping portion 255 of the imaging window region 248 over the hypotube region 250. A proximal section 256 of the hypotube region 250 may be free of slots.

Figure 8:
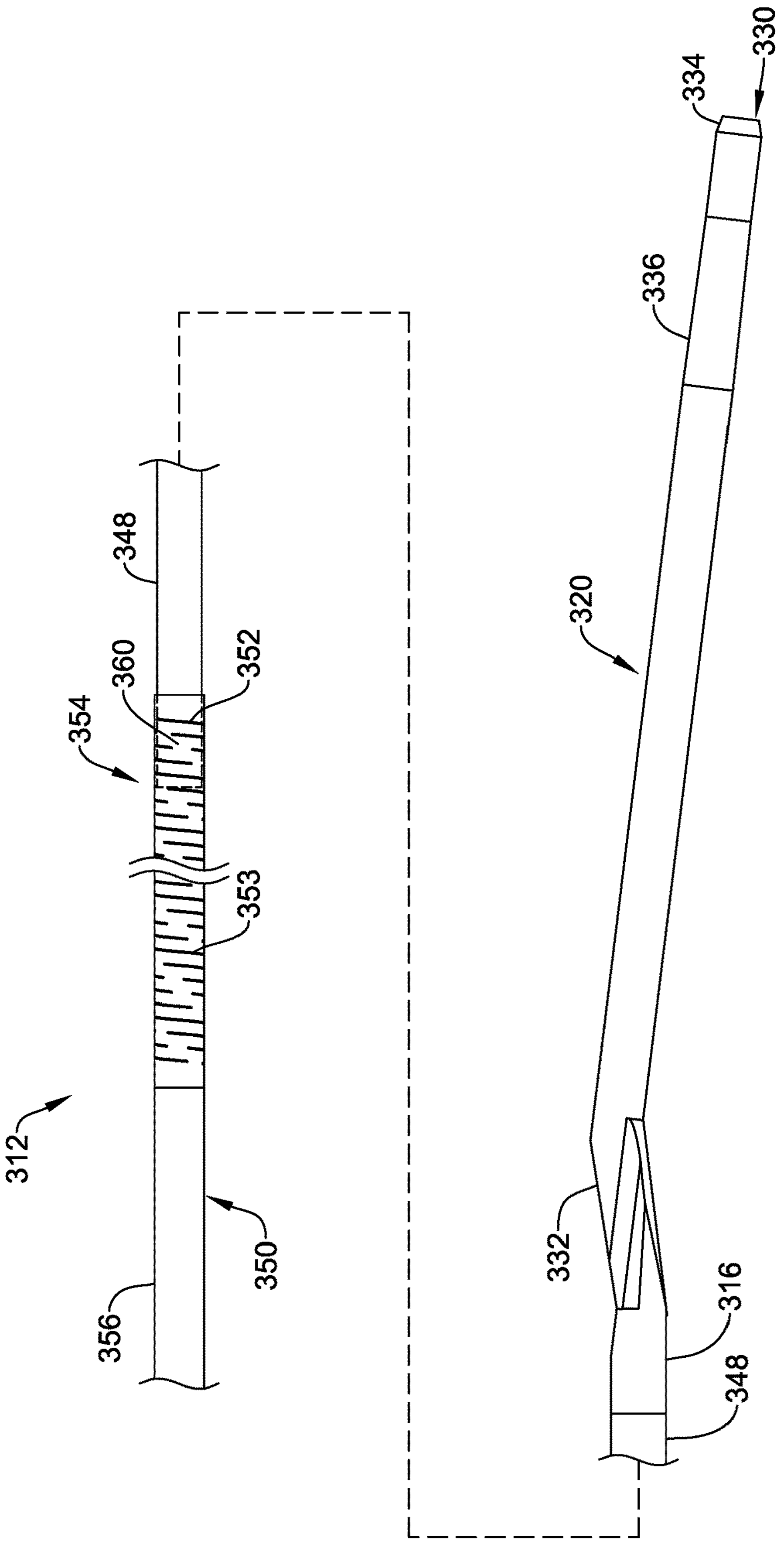
FIG. 8 is a partial cross-sectional side view of a portion of an example medical device.

FIG. 8 illustrates another example elongate shaft 312 that may be similar in form and function to other elongate shafts disclosed herein. The elongate shaft 312 may include a distal end region 316. A tip member 320 may be coupled to or otherwise disposed adjacent to the distal end region 316. The tip member 320 may include a guidewire lumen 330 having a guidewire exit port 332, an atraumatic distal end 334, one or more radiopaque markers 336, and/or other features. The elongate shaft 312 may include an imaging window region 348 and a hypotube region 350. The hypotube region 350 may include a slotted portion 353 having a plurality of slots 352 formed therein. A joint 354 is formed between the hypotube region 350 and the imaging window region 348. In the example shown in FIG. 8, the joint 354 is formed by inserting a proximal insertion region 360 into the hypotube region 350. In some instances, the inner surface and/or outer surface of the slotted section 353 may include a sleeve, coating, and/or seal that may close off or seal slots 352. A proximal section 356 of the hypotube region 350 may be free of slots.

The materials that can be used for the various components of the medical device 10 (and/or other devices disclosed herein) and the various tubular members disclosed herein may include those commonly associated with medical devices. For simplicity purposes, the following discussion refers to the elongate shaft 12 and other components of the medical device 10. However, this is not intended to limit the devices and methods described herein, as the discussion may be applied to other similar tubular members and/or components of tubular members or devices disclosed herein.

The elongate shaft 12 and/or other components of the medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MRI) compatibility is imparted into the medical device 10. For example, the medical device 10, or portions thereof, may be made of a material that does not substantially distort the image and create substantial artifacts (e.g., gaps in the image). Certain ferromagnetic materials, for example, may not be suitable because they may create artifacts in an MRI image. The medical device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An intravascular imaging device, comprising:
a catheter shaft assembly including a telescoping assembly and a catheter body;
wherein the catheter body includes a hypotube region, an imaging window region, and a distal end region having a guidewire lumen formed therein;
wherein the imaging window region and the hypotube region are coupled together at an overlapping joint;
wherein at least a portion of the hypotube region has a plurality of slots formed therein;
wherein the plurality of slots includes a first group of two or more slots disposed at a first axial location and a second group of two or more slots disposed at a second axial location spaced apart from the first axial location; and
an imaging core disposed within the catheter shaft assembly.

2. The intravascular imaging device of claim 1, wherein the imaging core is translatable within the catheter shaft assembly.

3. The intravascular imaging device of claim 1, wherein the imaging core includes an ultrasound transducer.

4. The intravascular imaging device of claim 1, wherein the imaging core includes an optical coherence tomography imaging device.

5. The intravascular imaging device of claim 1, wherein a distal portion of the hypotube region has the plurality of slots formed therein.

6. The intravascular imaging device of claim 1, wherein the plurality of slots are disposed along a section of the hypotube region that is 5-50 cm from a distal end of the hypotube region.

7. The intravascular imaging device of claim 1, wherein the plurality of slots are disposed along a section of the hypotube region that is 8-39 cm from a distal end of the hypotube region.

8. The intravascular imaging device of claim 1, wherein a proximal portion of the hypotube region is free of slots.

9. The intravascular imaging device of claim 1, wherein at least some of the slots of the plurality of slots lie within a plane that is substantially normal to a longitudinal axis of the hypotube region.

10. The intravascular imaging device of claim 1, wherein the plurality of slots are arranged in a helical pattern.

11. The intravascular imaging device of claim 1, wherein a proximal end region of the imaging window region is disposed along an outer surface of the hypotube region.

12. The intravascular imaging device of claim 1, wherein a proximal end region of the imaging window region is disposed along an inner surface of the hypotube region.

13. The intravascular imaging device of claim 1, wherein a proximal end of the imaging window region abuts a distal end of the hypotube region.

14. The intravascular imaging device of claim 13, wherein a sleeve is disposed over the proximal end of the imaging window and the distal end of the hypotube region.

15. An intravascular imaging device, comprising:

a catheter shaft assembly including a telescoping assembly and a catheter body;

wherein the catheter body includes a hypotube attached to the telescoping region, an imaging window region extending distally from the hypotube, and a distal end region having a guidewire lumen formed therein;

wherein a proximal end region of the imaging window region overlaps with a distal end region of the hypotube;

wherein the hypotube has a distal region having plurality of slots formed therein and a proximal region free from slots; and an imaging core disposed within the catheter shaft assembly.

16. The intravascular imaging device of claim 15, wherein a proximal end region of the imaging window region is disposed along an outer surface of the hypotube.

17. The intravascular imaging device of claim 15, wherein the plurality of slots are arranged so that at least some of the slots lie within a plane that is substantially normal to a longitudinal axis of the hypotube.

18. The intravascular imaging device of claim 15, wherein the plurality of slots are arranged in a helical pattern.

19. The intravascular imaging device of claim 15, wherein the plurality of slots are arranged in a spiral pattern.

20. A method for imaging a blood vessel, the method comprising:

disposing an intravascular imaging device within a blood vessel, the intravascular imaging device comprising:

a catheter shaft assembly including a telescoping assembly and a catheter body, wherein the catheter body includes a hypotube attached to the telescoping region, an imaging window region extending distally from the hypotube, and a distal end region having a guidewire lumen formed therein, wherein the hypotube has a distal region having plurality of slots formed therein and a proximal region free from slots, wherein a proximal end region of the imaging window region overlaps with the distal region of the hypotube, and an imaging core disposed within the catheter shaft assembly; and translating the imaging core relative to the catheter shaft.

* * * * *